(12) United States Patent
Hashino et al.

(10) Patent No.: US 9,278,035 B2
(45) Date of Patent: *Mar. 8, 2016

(54) INDIVIDUALLY PACKAGED PRODUCT

(75) Inventors: Akira Hashino, Kagawa (JP); Yuki Noda, Kagawa (JP); Shinpei Komatsu, Kagawa (JP); Hideyuki Kinoshita, Kagawa (JP)

(73) Assignee: Unicharm Corporation, Ehime (JP)

( * ) Notice: Subject to any disclaimer, the term of this patent is extended or adjusted under 35 U.S.C. 154(b) by 169 days.

This patent is subject to a terminal disclaimer.

(21) Appl. No.: 13/876,549

(22) PCT Filed: Sep. 22, 2011

(86) PCT No.: PCT/JP2011/072493
§ 371 (c)(1),
(2), (4) Date: Mar. 28, 2013

(87) PCT Pub. No.: WO2012/043778
PCT Pub. Date: Apr. 5, 2012

(65) Prior Publication Data
US 2013/0190711 A1 Jul. 25, 2013

(30) Foreign Application Priority Data
Sep. 30, 2010 (JP) ................. 2010-223072

(51) Int. Cl.
*A61F 13/551* (2006.01)
*A61F 13/84* (2006.01)

(52) U.S. Cl.
CPC ..... *A61F 13/5514* (2013.01); *A61F 2013/8497* (2013.01)

(58) Field of Classification Search
CPC ............ B65D 2203/00; B65D 2203/02; A61F 13/5514; A61F 13/55135; A61F 13/5513; A61F 13/55145; A61B 19/026
USPC .................. 206/440, 438, 459.5; 604/385.02, 604/385.05
See application file for complete search history.

(56) References Cited

U.S. PATENT DOCUMENTS

| | | | |
|---|---|---|---|
| 5,413,568 A * | 5/1995 | Roach et al. ................ | 604/358 |
| 6,168,582 B1 * | 1/2001 | Hasegawa ................ | 604/385.02 |
| 6,186,993 B1 * | 2/2001 | Toyoshima et al. ........ | 604/385.02 |
| 6,520,330 B1 * | 2/2003 | Batra ............................ | 206/494 |
| 8,231,590 B2 * | 7/2012 | Zander et al. ............ | 604/385.01 |

(Continued)

FOREIGN PATENT DOCUMENTS

| | | |
|---|---|---|
| CN | 1895197 A | 1/2007 |
| JP | U 57-136322 | 8/1982 |

(Continued)

OTHER PUBLICATIONS

European Search Report from corresponding European application No. 11829331.5 dated Sep. 11, 2014 (6 pgs).

(Continued)

*Primary Examiner* — Steven A. Reynolds
(74) *Attorney, Agent, or Firm* — Brinks Gilson & Lione (57) ABSTRACT

An individually wrapped absorbent article that is wrapped in a wrapping sheet wherein the wrapping sheet has a colored part on the inner surface on the side of the absorbent article, and the colored part of the wrapping sheet can be seen from the outside of the individually wrapped product but the absorbent article cannot be seen from the outside of the individually wrapped product.

16 Claims, 8 Drawing Sheets

(56) References Cited

U.S. PATENT DOCUMENTS

| | | | |
|---|---|---|---|
| 2004/0015145 A1* | 1/2004 | Miura et al. ................. 604/367 |
| 2005/0145523 A1 | 7/2005 | Zander et al. |
| 2005/0154365 A1* | 7/2005 | Zander et al. ............ 604/385.04 |
| 2006/0025739 A1* | 2/2006 | DiPalma et al. .......... 604/385.02 |
| 2006/0137568 A1* | 6/2006 | MacDonald et al. ...... 106/31.13 |
| 2007/0179467 A1 | 8/2007 | Shimizu et al. |
| 2008/0212903 A1* | 9/2008 | Germanow et al. ............. 383/42 |
| 2009/0105681 A1* | 4/2009 | Chicoine et al. ......... 604/385.02 |
| 2010/0286645 A1* | 11/2010 | MacDonald et al. .... 604/385.02 |
| 2011/0028931 A1* | 2/2011 | Fung ........................ 604/385.02 |
| 2011/0034897 A1* | 2/2011 | Nomoto et al. .......... 604/385.02 |
| 2011/0270208 A1* | 11/2011 | Miura et al. ............. 604/385.02 |
| 2012/0283680 A1* | 11/2012 | Zander et al. ................. 604/365 |
| 2012/0310201 A1* | 12/2012 | Oates ....................... 604/385.02 |

FOREIGN PATENT DOCUMENTS

| | | |
|---|---|---|
| JP | A 8-322882 | 12/1996 |
| JP | H 07-130593 | 12/1996 |
| JP | 2003-199786 A | 7/2003 |
| JP | 3617552 B | 11/2004 |
| JP | 2005-103065 A | 4/2005 |
| JP | A 2006-223757 | 8/2006 |
| JP | 2007-518481 A | 7/2007 |
| JP | 2008-080046 A | 4/2008 |
| JP | 2008-161249 A | 7/2008 |
| JP | 2009-178275 A | 8/2009 |
| WO | WO 2005/065605 A1 | 7/2005 |

OTHER PUBLICATIONS

International Search Report from corresponding PCT application No. PCT/JP2011/072493 dated Dec. 20, 2011 (4 pgs).

* cited by examiner

INDIVIDUALLY PACKAGED PRODUCT

RELATED APPLICATION

This application is a 35 U.S.C. §371 national phase filing of International Patent Application No. PCT/JP2011/072493, filed Sep. 22, 2011, through which and to which priority is claimed under 35 U.S.C. §119 to Japanese Patent Application No. 2010-223072, filed Sep. 30, 2010.

TECHNICAL FIELD

The present disclosure relates to an individually packaged product wherein an absorbent article is wrapped with a packaging sheet.

BACKGROUND ART

Individually packaged products are known which have absorbent articles, such as sanitary napkins, panty liners and paper diapers wrapped with individual packaging sheets. Individual packaging of the absorbent articles allows each of the absorbent articles to be conveniently and hygienically carried.

In the individually packaged product, it is usually the case that the absorbent article inside can be seen through the individually packaged product, or it is apparent that it is an individual packaged absorbent article, and therefore in order to disguise its sanitary nature, the individually packaged product is usually further placed in a pouch and encased in a bag or the like.

Therefore, it is preferred for an absorbent article housed in an individually packaged product to not be recognizable at a glance.

Thinner individually packaged products have also been developed as such individually packaged products, and are commercially available as products that neatly fit in bags and pockets and can be easily carried around.

In such thin individually packaged products, the entire outer surface of the individually packaged product is coated with a colored material so that the housed absorbent article is not recognizable at a glance.

Also, PTLs 1-4 are examples of individually packaged products wherein sections other than the outer surface of the packaging sheet are colored. In PTLs 1-3 there are described individually packaged products of absorbent articles in which the release layers are colored, while PTL 4 describes an individually packaged product of an absorbent article in which a drawing design is printed on the back sheet.

CITATION LIST

Patent Literature

PTL 1 Japanese Unexamined Patent Publication No. 8-322882
PTL 2 Japanese Unexamined Patent Publication No. 2006-223757
PTL 3 Japanese Patent No. 3617552
PTL 4 Japanese Unexamined Patent Publication No. 2003-199786

SUMMARY OF INVENTION

Technical Problem

However, when the outer surface of an individually packaged product is coated with a colored material, problems, such as color transfer, where colors of the colored material become transferred to adjacent objects, can occur due to abrasion in the manufacturing line during production, abrasion between individually packaged products during distribution or abrasion inside the bag after purchase. Also, since the individually packaged products described in PTLs 1-4 are not colored to an extent that hides the absorbent article in the individually packaged product, the interior absorbent article can be seen through the outer surface of the individually packaged product, and it has been necessary to further place it in a pouch or house it in a bag or the like, in order to prevent it from being seen by other people.

It is therefore an object of the present disclosure to provide an individually packaged product that can be placed in a bag, pocket or the like and easily carried, so that the absorbent article is poorly visible through the outer surface of the individually packaged product, and color transfer does not easily take place with other individually packaged products.

Solution to Problem

As a result of diligent research directed toward solving the problems described above, the present inventors have found an individually packaged product in which an absorbent article is wrapped with a packaging sheet, wherein the packaging sheet has a colored part on an inner surface on the absorbent article side, and the colored part is visible through an outer surface of the individually packaged product, but the absorbent article is not visible through the outer surface of the individually packaged product.

Specifically, the present disclosure relates to the following aspects.

[Aspect 1]
An individually packaged product in which an absorbent article is wrapped with a packaging sheet, wherein the packaging sheet has a colored part on an inner surface on the absorbent article side, and the colored part is visible through an outer surface of the individually packaged product, but the absorbent article is not visible through the outer surface of the individually packaged product.

[Aspect 2]
The individually packaged product according to aspect 1, wherein the absorbent article has a pressure-sensitive adhesive part on the non-skin-contact surface, the absorbent article is attached to the inner surface of the packaging sheet sandwiching the pressure-sensitive adhesive part, and the absorbent article and packaging sheet is formed by folding the absorbent article inward.

[Aspect 3]
The individually packaged product according to aspect 2, wherein the colored part on the inner surface of the packaging sheet further has a detaching function which allows the absorbent article to be easily detached from the packaging sheet.

[Aspect 4]
The individually packaged product according to any one of aspects 1 to 3, wherein the colored part on the inner surface of the packaging sheet is formed by coating the inner surface of the packaging sheet with a single colored material while varying the amount per unit area, and the colored part on the inner surface of the packaging sheet forms a predetermined pattern on the inner surface of the packaging sheet.

[Aspect 5]
The individually packaged product according to any one of aspects 1 to 3, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

[Aspect 6]

The individually packaged product according to any one of aspects 1 to 5, wherein the packaging sheet has the colored part over the entire inner surface on the absorbent article side.

[Aspect 7]

The individually packaged product according to aspect 2 or 3, wherein a release part covers a surface of the colored part on the inner surface of the packaging sheet that contacts with a pressure-sensitive adhesive part.

[Aspect 8]

The individually packaged product according to aspect 2 or 3, wherein a release sheet is bonded to a surface of the colored part on the inner surface of the packaging sheet that contacts with the pressure-sensitive adhesive part.

[Aspect 9]

The individually packaged product according to any one of aspects 1 to 8, wherein the packaging sheet further has a colored part on an outer surface on the side opposite the inner surface.

[Aspect 10]

The individually packaged product according to aspect 9, wherein the colored part on the outer surface of the packaging sheet has a smaller area than the area of the colored part on the inner surface of the packaging sheet.

[Aspect 11]

The individually packaged product according to any one of aspects 1 to 10, wherein the absorbent article further has a colored part on an outer surface of the absorbent article, on the packaging sheet side, the packaging sheet has the colored part on the inner surface of the packaging sheet and optional colored part on the outer surface of the packaging sheet so that the colored part on the outer surface of the absorbent article is not visible through the outer surface of the individually packaged product.

Advantageous Effects of Invention

The individually packaged product of the disclosure can be placed in a bag, pocket or the like and easily carried, so that the absorbent article is poorly visible through the outer surface of the individually packaged product, and color transfer does not easily take place with other individually packaged products.

DESCRIPTION OF EMBODIMENTS

The individually packaged product of the disclosure will now be explained in detail.

Figure 1:
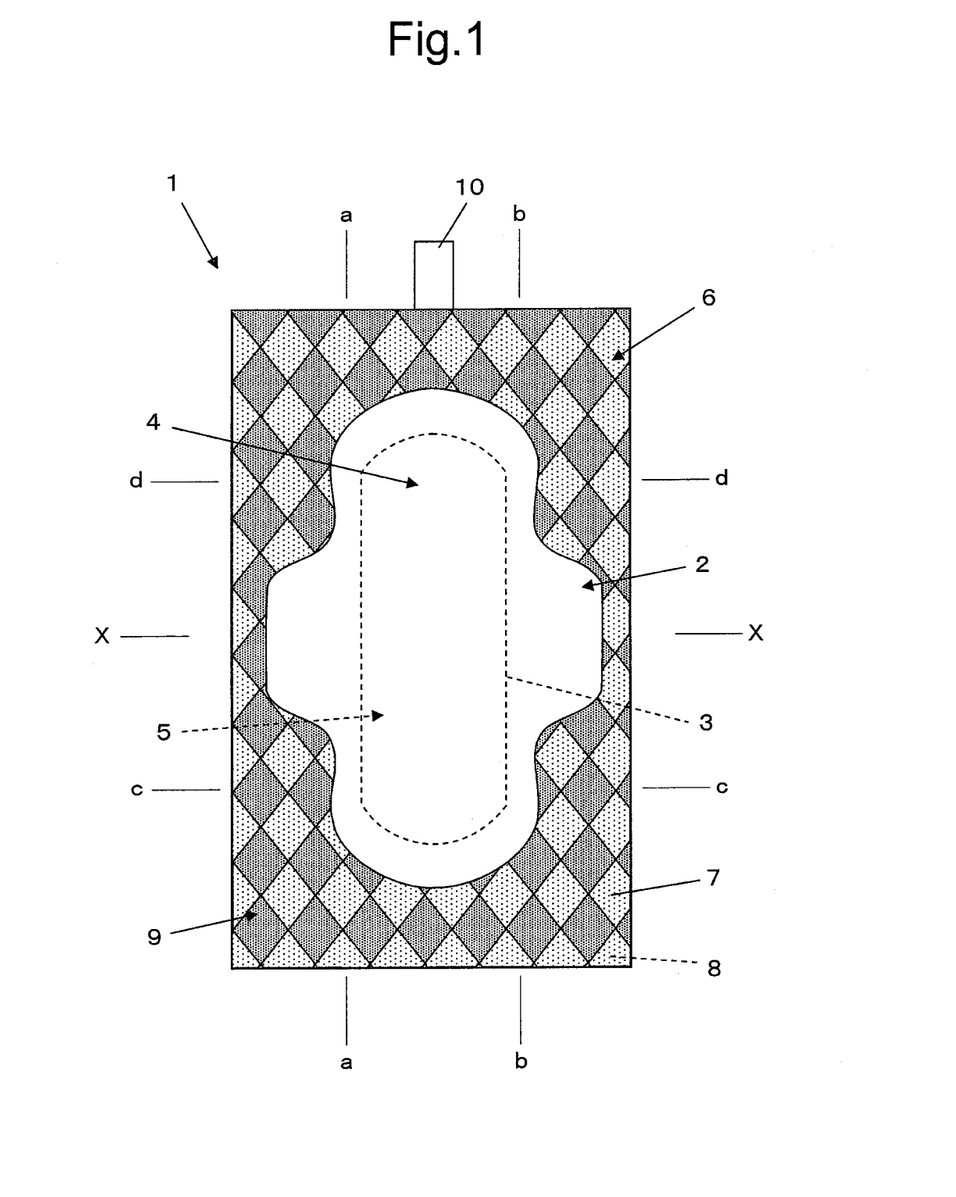
FIG. 1 is an expanded view of an embodiment of the individually packaged product of the disclosure.

FIG. 1 is an expanded view of an embodiment of the individually packaged product of the disclosure.

The individually packaged product 1 shown in FIG. 1 comprises an absorbent article 2, as a sanitary napkin with an absorbent body 3, a packaging sheet 6 packaging the absorbent article 2, and a tab 10. The absorbent article 2 has a pressure-sensitive adhesive part (not shown) on the non-skin-contact surface 5, the absorbent article 2 being attached to the inner surface 7 of the packaging sheet 6 and sandwiching the pressure-sensitive adhesive part (not shown), while the absorbent article 2 and packaging sheet 6 are folded with the absorbent article 2 facing inward, thereby forming an individually packaged product 1.

The packaging sheet 6 has a first colored part 9, and on the inner surface 7 of the absorbent article 2, the first colored part 9 is visible through the outer surface of the individually packaged product 1 while the absorbent article 2 is not visible through the outer surface of the individually packaged product 1. The skin contact surface 4 of the absorbent article and the outer surface 8 of the packaging sheet 6 are shown in FIG. 1.

As used herein, the phrase "colored part on the inner surface of the packaging sheet" may be referred to as "first colored part" to differentiate it from the other colored parts.

The denotations a-a, b-b, c-c and d-d in FIG. 1 are the folding lines of the individually packaged product 1.

As used herein, "the absorbent article is not visible through the outer surface of the individually packaged product" means that when the individually packaged product of the disclosure is casually observed, it is not obvious that an absorbent article is contained in the individually packaged product. Since it is assumed that the individually packaged product of the disclosure is to be placed in a bag, pocket or the like and simply carried, it is essential that other persons cannot discern that an absorbent article is contained in the individually packaged product when it is casually removed from the bag or pocket or when the contents of the bag are viewed under such conditions.

Thus, cases where it can be discerned that an absorbent article is contained in the individually packaged product by close observation of the individually packaged product of the disclosure, the absorbent article contained in the individually packaged product being visible through thin sections of the pattern or an absorbent article-like object being discernible through the opening of the individual package, are not included in the description "visible".

In order to render the absorbent article not visible through the outer surface of the individually packaged product, the packaging sheet may have a first colored part over the entire inner surface, for example.

Also, in order to render the absorbent article not visible through the outer surface of the individually packaged product, the visible light transmittance of the packaging sheet with the first colored part and the optional second colored part is preferably no greater than about 75%, more preferably no greater than about 65% and even more preferably no greater than about 60%. If the transmittance exceeds about 75%, the absorbent article may sometimes be visible through the outer surface of the individually packaged product.

The lower limit for the visible light transmittance is about 0%. For example, an embodiment in which the visible light transmittance of the packaging sheet material itself is high but the masking property of the first colored part is high, resulting in a visible light transmittance of 0%, has the colored part visible through the outer surface of the individually packaged product, but since the absorbent article is not visible through the outer surface of the individually packaged product, such an embodiment is included in the embodiment of the disclosure.

Figure 2:
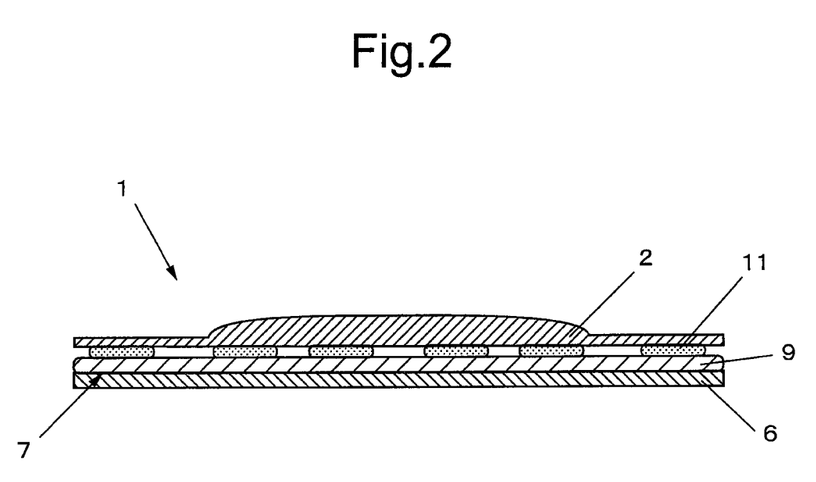
FIG. 2 is a cross-sectional view of the individually packaged product 1 in FIG. 1, along cross-section X-X.

FIG. 2 is a cross-sectional view of the individually packaged product 1 in FIG. 1, along cross-section X-X. In the individually packaged product 1 shown in FIG. 2, the packaging sheet 6 has a first colored part 9 on the inner surface 7, and the absorbent article 2 is attached to the inner surface 7 of the packaging sheet 6, sandwiching a pressure-sensitive adhesive part 11.

Figure 3:
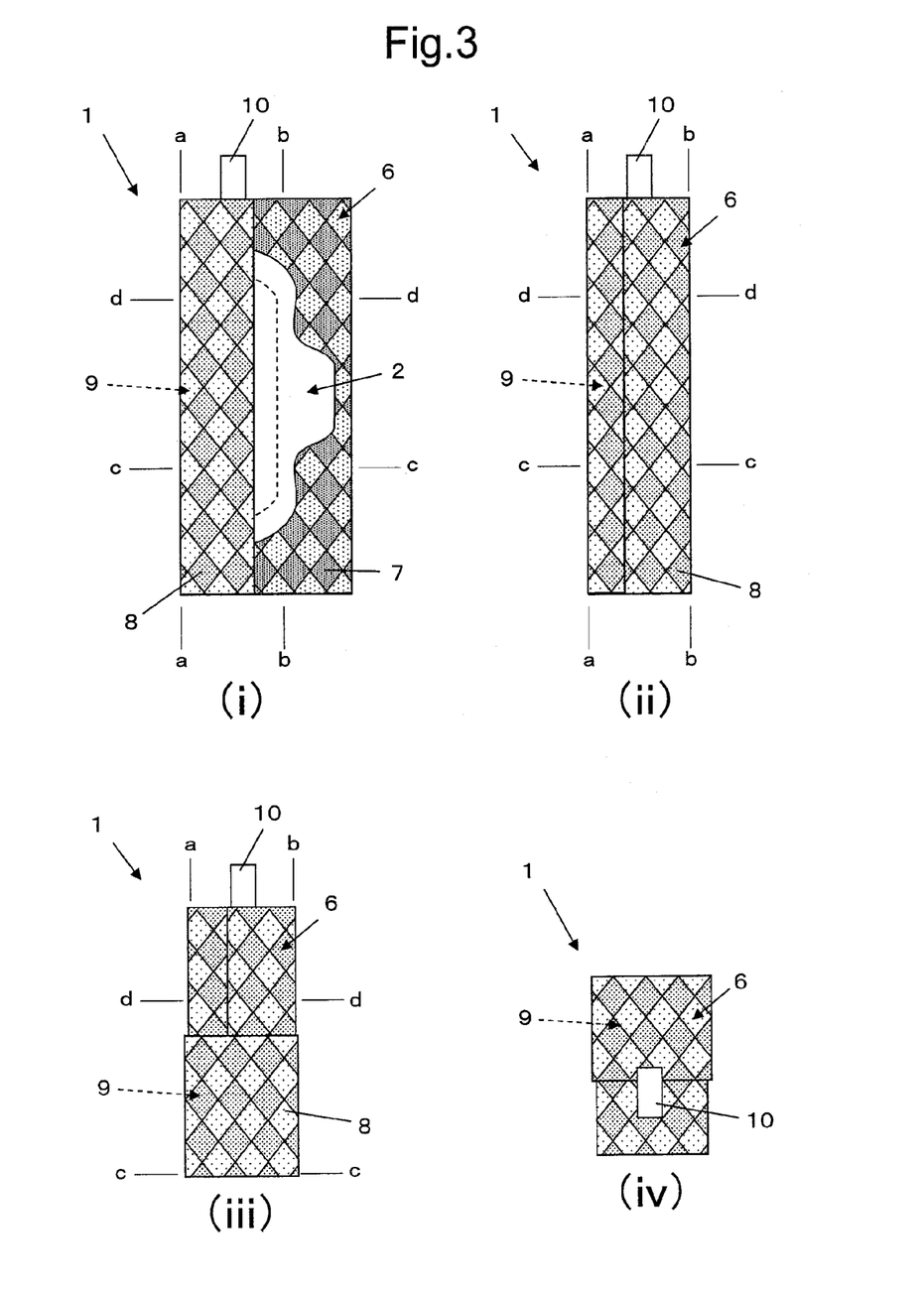
FIG. 3 is a drawing illustrating a manner of folding the individually packaged product shown in FIG. 1.

FIG. 3 is a drawing illustrating a folded structure for the individually packaged product shown in FIG. 1 and FIG. 2. In the individually packaged product 1 shown in FIG. 3, the absorbent article 2 is attached to the inner surface 7 of the packaging sheet 6, sandwiching a pressure-sensitive adhesive part (not shown). The absorbent article 2 and packaging sheet 6 are first folded along folding line a-a, as shown in FIG. 3(i), with the left-hand region of the absorbent article 2 and packaging sheet 6 left of the folding line a-a, being folded onto the region defined by folding line a-a and folding line b-b.

In the left-hand region, the first colored part 9 can be seen through the packaging sheet 6.

Next, as shown in FIG. 3(ii), the right-hand region of the absorbent article 2 and packaging sheet 6 right of the folding line b-b is folded along folding line b-b over the outer surface 8 of the packaging sheet 6 in the left-hand region, in the middle region.

In the left-hand region and right-hand region, the first colored part 9 can be seen through the packaging sheet 6.

Similarly, as shown in FIG. 3(iii), the lower region at the lower end of the absorbent article 2 and packaging sheet 6 is folded along the folding line c-c, onto the middle region defined by folding line c-c and folding line d-d, and then as shown in FIG. 3(iv), the upper region at the upper end of the absorbent article 2 and packaging sheet 6 is folded along folding line d-d onto the middle region, and is fixed with a tab 10, thereby forming an individually packaged product 1.

In the individually packaged product 1 illustrated in FIG. 3(iv), the first colored part 9 is entirely visible through the packaging sheet 6.

When the individually packaged product of the disclosure has a folded structure, the folded structure may be appropriately fixed using a tab, hot-melt adhesive or the like.

As seen in FIG. 3(iv), the individually packaged product of the disclosure has the first colored part visible through the outer surface of the individually packaged product, but the absorbent article is not visible through the outer surface of the individually packaged product.

In the embodiment illustrated in FIGS. 1 to 3, the first colored part is formed over the entire inner surface of the packaging sheet, but the individually packaged product of the disclosure does not particularly need to have the first colored part formed over the entire inner surface of the packaging sheet, so long as the absorbent article is not visible through the outer surface of the individually packaged product. For example, in the packaging sheet, the first colored part may be formed only in the region of the individually packaged product that is externally visible in the individually packaged product, such as the region defined by folding line a-a and folding line b-b in FIG. 3.

In FIG. 1, the absorbent article 2 is attached to the inner surface 7 of the packaging sheet 6 sandwiching a pressure-sensitive adhesive part, but in the embodiment illustrated in FIG. 1, wherein the absorbent article is attached to the inner surface of the packaging sheet, the absorbent article inside the individually packaged product moves minimally in directions different from the packaging sheet, i.e. the absorbent article undergoes little friction with the first colored part on the inner surface of the packaging sheet, and hence transfer of the colors of the first colored part on the inner surface of the packaging sheet to the absorbent article is minimal.

In FIG. 2, the individually packaged product 1 is formed by folding the absorbent article 2 and packaging sheet 6 four times, but according to the disclosure the absorbent article and/or packaging sheet do not need to be folded, or even if the absorbent article and/or packaging sheet are folded, there is no particular restriction on the number of folds.

Figure 4:
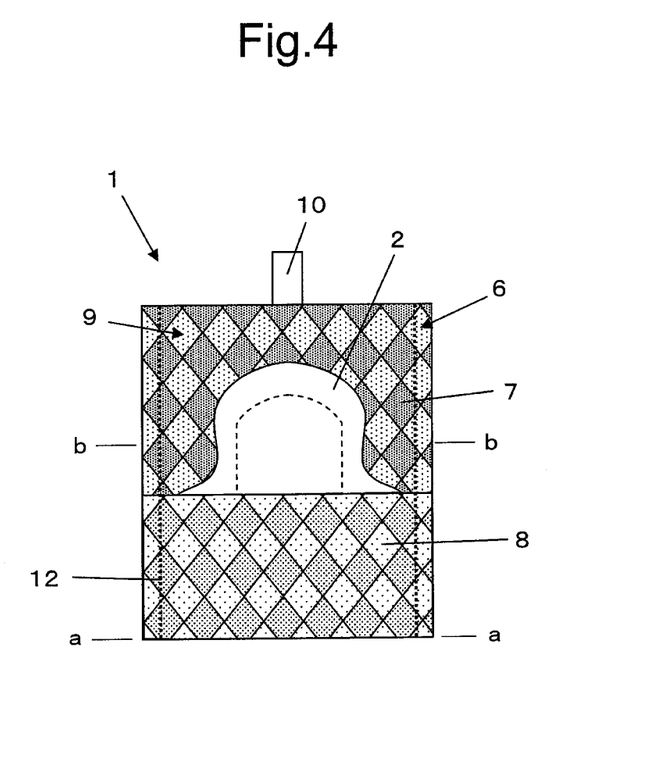
FIG. 4 is a drawing illustrating an example of a triple-fold individually packaged product.

FIG. 4 is a drawing illustrating an example of a triple-fold individually packaged product, as an embodiment of the individually packaged product of the disclosure. The individually packaged product 1 shown in FIG. 4 is formed by folding the absorbent article 2 and packaging sheet 6 at folding line a-a and folding line b-b, which are two folding lines perpendicular to the lengthwise direction, and by sealing the sides in the lengthwise direction at the heat seal 12, but it is shown with the tab 10 raised for ease of explanation.

In FIG. 1, the absorbent article 2 is attached to the inner surface 7 of the packaging sheet 6 sandwiching the pressure-sensitive adhesive part, but in the individually packaged product of the disclosure, the absorbent article is not limited to an embodiment in which the packaging sheet is attached to the inner surface.

Figure 5:
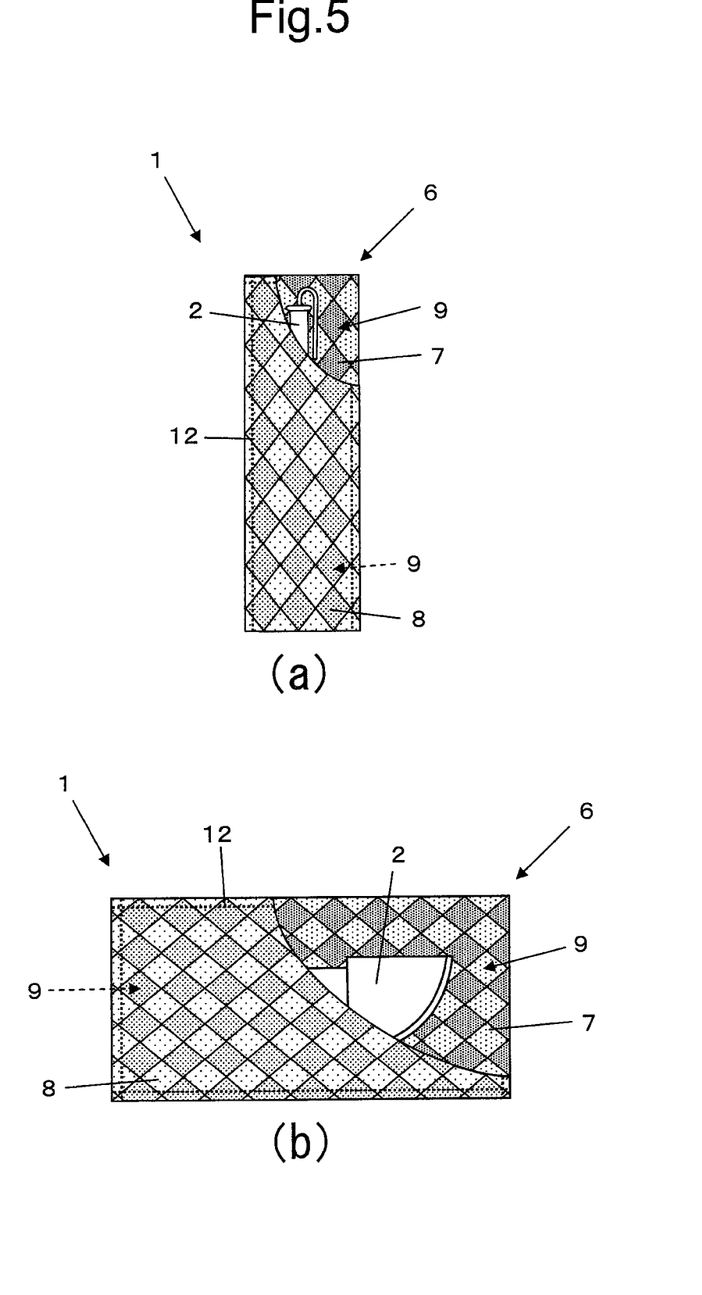
FIG. 5 is a drawing illustrating an embodiment of the individually packaged product of the disclosure.

FIG. 5 is a drawing illustrating an embodiment of the individually packaged product of the disclosure. FIG. 5 is an example of an individually packaged product in which the absorbent article is not attached to the inner surface of the packaging sheet.

FIG. 5(a) is an example of an individually packaged product in which the absorbent article is a tampon. In the individually packaged product 1 shown in FIG. 5(a), the absorbent article 2, which is a tampon, is disposed in the packaging sheet 6 which has been folded twice with the inner surface 7 bearing the first colored part 9 facing inward and the outer surface 8 facing outward, and the three sides other than the sections of the packaging sheet 6 that have been folded twice, are sealed with a heat seal 12, thereby forming the individually packaged product 1.

FIG. 5(b) is an example of an individually packaged product in which the absorbent article is a labial pad. In the individually packaged product 1 shown in FIG. 5(b), the absorbent article 2, which is a labial pad, is disposed between two packaging sheets 6 with the inner surface 7 bearing the first colored part 9 facing inward and the outer surface 8 facing outward, and the four sides of the packaging sheet 6 are sealed with a heat seal 12, thereby forming the individually packaged product 1.

In the individually packaged products shown in FIG. 5, each individually packaged product of the disclosure has the first colored part visible through the outer surface of the individually packaged product, while the absorbent article is not visible through the outer surface of the individually packaged product.

In the embodiments shown in FIGS. 1 to 3, the first colored part 9 also has a detaching function which allows the absorbent article 2 to be easily detached from the packaging sheet 6. A first colored part having such a detaching function can be formed by covering the packaging sheet with a colored material comprising a coloring component, such as a pigment and/or dye, a release component, such as a silicone resin, fluorine resin or octadecyl isocyanate and an optional base resin, such as acryl or polyester.

The coloring component is preferably a pigment, in order to avoid color transfer caused by water wetting, and the pigment may be, for example, an inorganic pigment, such as cobalt oxide, titanium dioxide, titanium black or titanium yellow, an organic pigment, such as an azo-based pigment or phthalocyanine-based pigment, or a fluorescent pigment composed mainly of an oxide, sulfide, silicide, phosphate or tungstate of calcium, barium, magnesium, cadmium or the like.

The amount of the coloring component for exhibiting the effect of the disclosure will vary depending on the type, amount and size of the coloring component, and also depending on the colored part on the outer surface of the packaging sheet, described hereunder, but generally the coloring component will be present in the first colored part at between about 1 and about 30 mass %, preferably between about 2 and about 20 mass % and even more preferably between about 3 and about 10 mass %.

The colored material is preferably a curable material comprising a crosslinkable functional group, such as a thermosetting or radiation-curing material, for example, a UV curable material, so that the first colored part to be formed does not transfer its color to the absorbent article. Considering that the packaging sheet in which the first colored part is to be formed will usually be a sheet with a low melting point and/or glass transition temperature, the colored material is preferably a radiation-curing material, such as a UV curable material, which does not deform the packaging sheet.

As mentioned above, adding a detaching function to the first colored part provides advantages, such as lowering of production cost, since there is no step of separately providing the release part and release sheet, described below, increase in the production rate since there is no need to position the pressure-sensitive adhesive part and the release region, and reduction of waste, since there is no need for a release sheet.

The first colored part is not particularly restricted so long as the first colored part is visible through the outer surface of the individually packaged product while the absorbent article is not visible through the outer surface of the individually packaged product, and for example, it may have a single color, such as pink or sea-blue, or the first colored part may have a pattern.

The method for forming the first colored part on the inner surface of the release sheet is not particularly restricted, and for example, and when a first colored part with a single color is to be formed, the first colored part may be formed by coating the release sheet with the colored material using means, such as roll coating or spray coating.

The first colored part may also be formed on the inner surface of the release sheet by means, such as printing. Gravure printing, for example, may be used to coat the packaging sheet with a single colored material while varying the amount per unit area, to form a first colored part having a predetermined pattern. Means, such as gravure printing is advantageous from the viewpoint of production cost, since it allows a pattern to be formed from a single colored material by varying the amount per unit area.

Alternatively, means, such as screen printing or flexographic printing may be used to coat the packaging sheet with a plurality of colored materials with different colors, to form a first colored part having a predetermined pattern.

In the individually packaged product of the disclosure, the packaging sheet has a first colored part on the inner surface, the first colored part being visible through the outer surface of the individually packaged product, and the absorbent article being not visible through the outer surface of the individually packaged product. In order for the first colored part to have this function, the first colored part must have a consistent masking property that conceals the absorbent article inside it. The masking property is mainly determined by the type, amount and size of the coloring components, such as the pigment and/or dye in the first colored part, and generally a consistent masking property can be obtained by including the coloring component in the amount specified above.

In the embodiments shown in FIGS. 1 to 3, the first colored part has a detaching function which allows the absorbent article to be easily detached from the packaging sheet, but the individually packaged product of the disclosure may further include a release part or release sheet when the first colored part does not have a detaching function.

Figure 6:
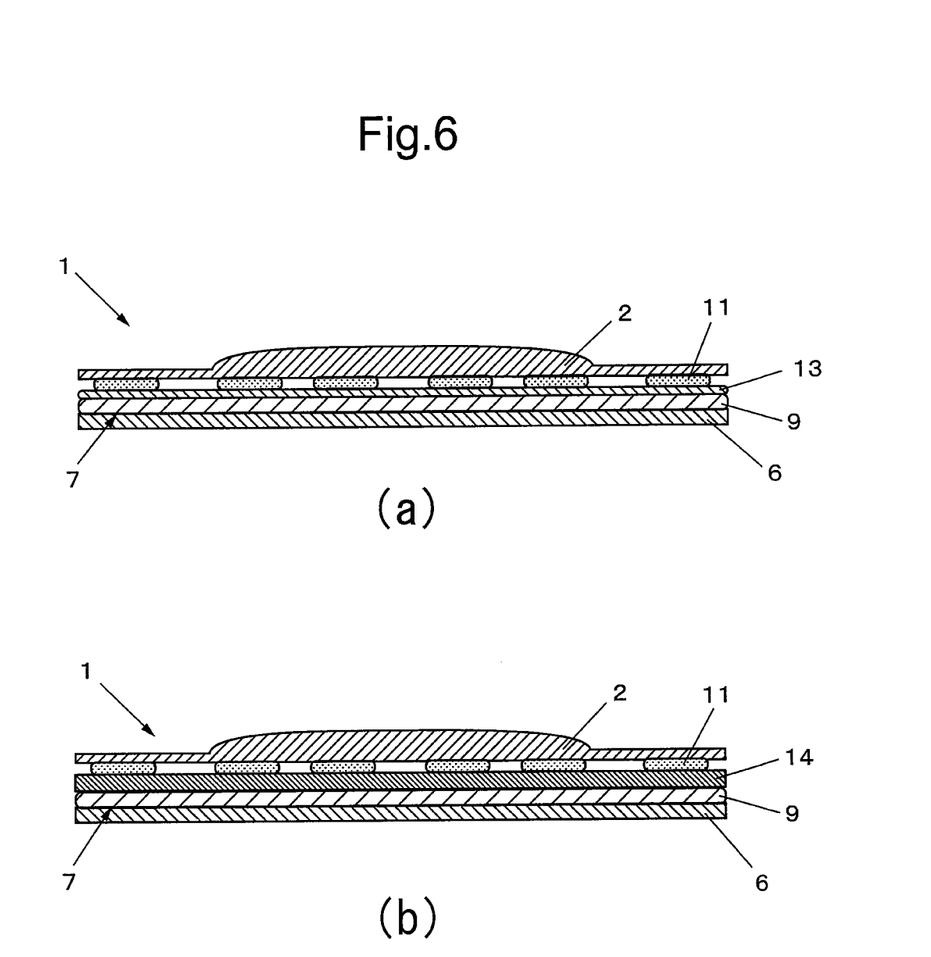
FIG. 6 is a drawing illustrating an example of an individually packaged product comprising a release part or a release sheet.

FIG. 6 is a drawing illustrating an example of an individually packaged product comprising a release part or a release sheet.

In the individually packaged product 1 shown in FIG. 6(*a*), the packaging sheet 6 has a first colored part 9 on the inner surface 7, a release part 13 covering the first colored part 9, and the absorbent article 2 is attached to the inner surface 7 of the packaging sheet 6, sandwiching the release part 13 and a pressure-sensitive adhesive part 11.

The release part can be formed by means known in the industry, such as covering the first colored part with a release material comprising a release component, such as a silicone resin, fluorine resin or octadecyl isocyanate and an optional base resin, such as acryl or polyester, and attaching the absorbent article which has the pressure-sensitive adhesive part on the non-skin-contact surface, to the release part.

In the individually packaged product 1 shown in FIG. 6(*b*), the packaging sheet 6 has a first colored part 9 on the inner surface 7, a release sheet 14 being bonded on the first colored part 9, and the absorbent article 2 is attached to the inner surface 7 of the packaging sheet 6, sandwiching the release sheet 14 and pressure-sensitive adhesive part 11.

The releasable sheet may be a releasable sheet commonly used in the technical field, for example, a sheet with low surface energy, such as a sheet coated with a silicone-based compound or fluorine-based compound, or a TEFLON™ sheet.

In the embodiments illustrated in FIGS. 1 to 3, the packaging sheet does not have a colored part on the outer surface on the side opposite the inner surface, but the packaging sheet may have a colored part on the outer surface of the packaging sheet in the individually packaged product of the disclosure.

As used herein, the phrase "colored part on the outer surface of the packaging sheet" may be referred to as "second colored part" to differentiate it from the other colored parts.

Figure 7:
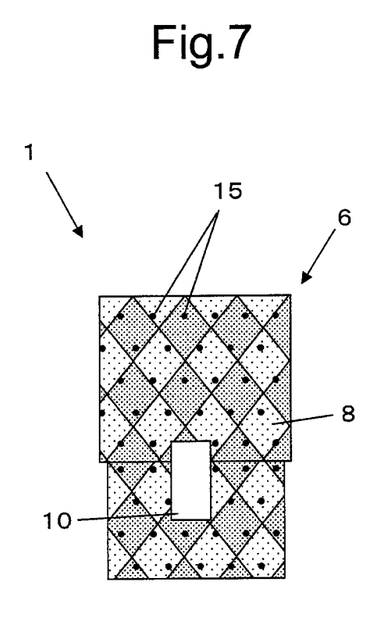
FIG. 7 is a drawing illustrating an example of an individually packaged product with a second colored part on the outer surface of the packaging sheet.

FIG. 7 is a drawing illustrating an example of an individually packaged product with a second colored part on the outer surface of the packaging sheet.

The individually packaged product 1 shown in FIG. 7 is formed by folding four times and attaching with a tab 10, as shown in FIG. 3, and the packaging sheet 6 has a second colored part 15 comprising a plurality of dots, arranged in a continuous manner at a fixed spacing on the outer surface 8.

The first colored part and second colored part may have the same pattern, or they may have different patterns, as shown in FIG. 7. When the individually packaged product contains a sanitary napkin, tampon, labial pad or panty liner as the absorbent article, the patterns of the first colored part and second colored part may be varied in order to lessen the feeling of melancholy during the menstruation period.

Also, if the second colored part is a smaller pattern with lower subjective brightness, the visual line of an observer will be led to the second colored part, so that the absorbent article in the individually packaged product may not be recognized.

The second colored part on the outer surface of the packaging sheet preferably has a smaller area than the area of the first colored part on the inner surface of the packaging sheet.

This is because if the area of the second colored part is increased, problems, such as color transfer, where colors of the colored material become transferred to adjacent objects, can occur due to abrasion in the manufacturing line during production, abrasion between individually packaged products during distribution, or abrasion inside the bag after purchase. Furthermore, in order to avoid impairing the design property of the individually packaged product of the disclosure, the second colored part preferably has a smaller area than the area of the first colored part.

Although the absorbent article does not have a colored part in each of the individually packaged products shown in FIGS. 1 to 3, the individually packaged product of the disclosure may be one in which the absorbent article also has a colored part on the outer surface of the absorbent article, on the outer surface of the packaging sheet side, and the packaging sheet may also have the first colored part and an optional second colored part so that the colored part on the outer surface of the absorbent article is not visible through the outer surface of the individually packaged product.

As used herein, the phrase "colored part on the outer surface of the absorbent article" may be referred to as "third colored part" to differentiate it from the other colored parts.

Figure 8:
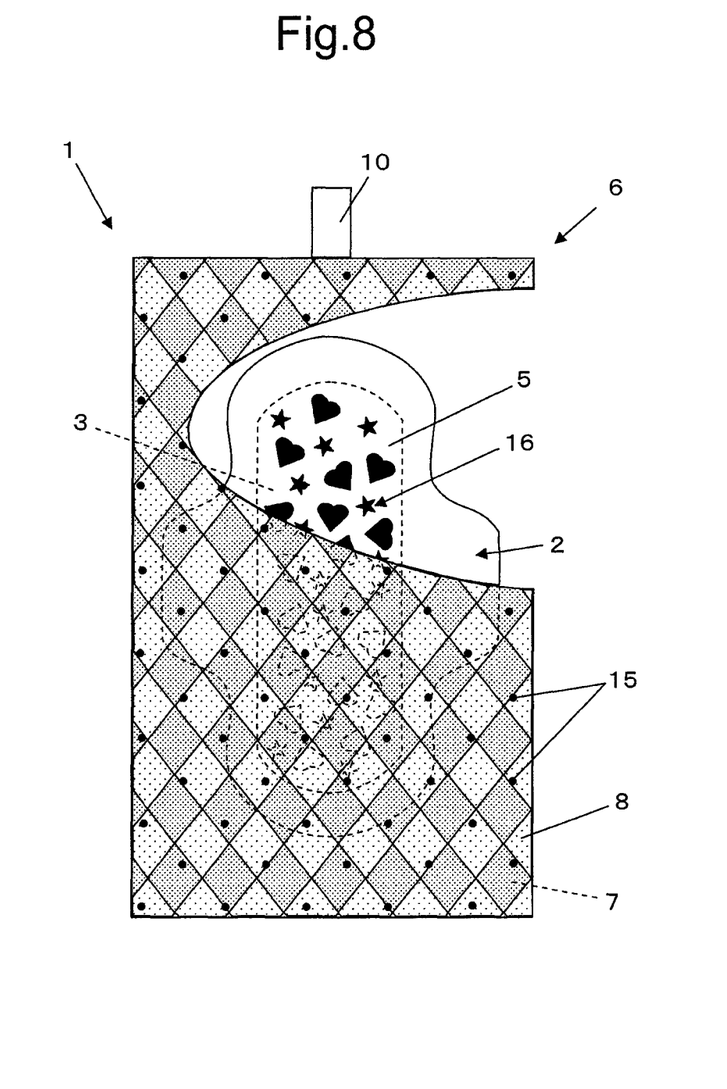
FIG. 8 is an expanded view of an embodiment of the individually packaged product of the disclosure.

FIG. 8 is an expanded view of an embodiment of the individually packaged product of the disclosure.

The individually packaged product 1 shown in FIG. 8 comprises an absorbent article 2, as a sanitary napkin with an absorbent body 3, a packaging sheet 6 packaging the absorbent article 2, and a tab 10. The absorbent article 2 has a pressure-sensitive adhesive part (not shown) on the non-skin-contact surface 5 which serves as the back sheet, and a third colored part 16 consisting of a predetermined pattern is formed on the non-skin-contact surface 5. In the individually packaged product 1 shown in FIG. 8, the packaging sheet 6 has a second colored part 15 having a plurality of dots arranged in a square zigzag fashion, on its outer surface 8.

In the individually packaged product 1 shown in FIG. 8, the absorbent article 2 is attached to the inner surface 7 of the packaging sheet 6, sandwiching the pressure-sensitive adhesive part (not shown), while the absorbent article 2 and packaging sheet 6 are folded with the absorbent article 2 facing inward, thereby forming an individually packaged product 1.

The third colored part will usually be attached to the non-skin-contact surface of the back sheet of a sanitary napkin or a winged reinforcing sheet, in order to reduce the feeling of melancholy during the menstrual period of the user. However, since awareness of the menstrual period may be emphasized when the third colored part can be seen through the outer surface of the individually packaged product before use, the third colored part is preferably not visible through the outer surface of the individually packaged product.

In order for the packaging sheet to have the first colored part and optional the second colored part so that the colored part on the outer surface of the absorbent article is not visible through the outer surface of the individually packaged product, for example, (i) the masking property of the first colored part and/or second colored part may be increased to physically block visibility of the third colored part through the exterior, (ii) the color of the first colored part and/or second colored part may be similar to the color of the third colored part to render the third colored part less apparent through the exterior, or (iii) the color saturation of the third colored part may be reduced to render the third colored part less apparent through the exterior.

The absorbent article to be used for the disclosure is not particularly restricted so long as it can be sold in a form that is individually packaged, and as examples there may be mentioned a sanitary napkin, panty liner, labial pad, paper diaper or tampon.

The packaging sheet to be used for the disclosure is not particularly restricted so long as it is one used in the technical field for individual packaging of absorbent articles, and examples include woven fabrics, nonwoven fabrics, felt, pile, films, sheets and laminates of the foregoing.

A coloring component, such as a pigment or dye may be added to the packaging sheet to alter the visible light transmittance, color or the like of the packaging sheet. By altering the visible light transmittance, color or the like of the packaging sheet, it is possible to change the appearance of the color, pattern or the like of the first colored part before and after the individually packaged product is opened, and to reduce melancholy during the menstrual period.

The pressure-sensitive adhesive parts used for the disclosure may employ a pressure-sensitive adhesive commonly used in the technical field, such as a hot-melt pressure-sensitive adhesive, which may be a polyolefinic (for example, polyethylene or polypropylene) hot-melt pressure-sensitive adhesive, an ethylene/vinyl acetate copolymer-based hot-melt pressure-sensitive adhesive, synthetic rubber-based (for example, styrene-based copolymer, butadiene-based copolymer or isoprene-based copolymer) hot-melt pressure-sensitive adhesive, an acrylic resin-based pressure-sensitive adhesive, or a polyvinyl alcohol-based pressure-sensitive adhesive.

EXAMPLES

The disclosure will now be explained by examples, with the understanding that the disclosure is not meant to be limited to the examples.

Example 1

Pink, blue and yellow colored materials were coated onto a polyethylene film using a gravure printer, varying the cell sizes, to form packaging sheets No. 1 to 12.

The transmittances of packaging sheets No. 1 to 12 were measured.

The transmittances were measured using an A300/ZE-2000 flicker photometric color difference meter by Nippon Denshoku Industries Co., Ltd.

The same packaging sheet was measured 5 times at different locations, and the mean value was recorded as the result. The results are shown in Table 1.

Example 2

A commercially available sanitary napkin was attached to each of packaging sheets Nos. 1 to 12 with a pressure-sensitive adhesive, and the sanitary article was folded inward as shown in FIG. 3 to form an individually packaged product. Each individually packaged product was casually observed by ten participants, and it was judged whether or not the sanitary napkin in the individually packaged product was visible. The results are shown in Table 1. A value of 10% visibility means that one participant judged the sanitary napkin in the individually packaged product to be visible.

Example 3

Eight different commercially available individual packaged sanitary napkins (commercial products A-H) were acquired, and the transmittances of the packaging sheets (Nos. 13 to 20) were measured in the same manner as Example 1. The results are shown in Table 1.

The packaging sheets of commercially available individually packaged sanitary napkins are either provided with colored parts on the outer surfaces of the packaging sheets, or the packaging sheets themselves are colored, or combinations of these methods are used.

Example 4

In packaging sheets Nos. 13 to 20, the same type of absorbent article used in Example 2 is attached with a pressure-sensitive adhesive, and the visibility was evaluated in the same manner as Example 2. The results are shown in Table 1.

TABLE 1

| No. | Color | Transmittance (%) | Visibility |
|---|---|---|---|
| 1 | Pink | 56.9 | 0% |
| 2 | Pink | 52.4 | 0% |
| 3 | Pink | 48.9 | 0% |
| 4 | Pink | 45.0 | 0% |
| 5 | Yellow | 60.5 | 0% |
| 6 | Yellow | 59.0 | 0% |
| 7 | Yellow | 57.1 | 0% |
| 8 | Yellow | 53.7 | 0% |
| 9 | Blue | 56.7 | 0% |
| 10 | Blue | 53.3 | 0% |
| 11 | Blue | 45.6 | 0% |
| 12 | Blue | 43.9 | 0% |
| 13 | White (Commercial product A) | 74.5 | 20% |
| 14 | Yellow (Commercial product B) | 54.8 | 0% |
| 15 | Green (Commercial product C) | 54.7 | 0% |
| 16 | Pink (Commercial product D) | 54.6 | 0% |
| 17 | Blue (Commercial product E) | 54.3 | 0% |
| 18 | Orange (Commercial product F) | 50.2 | 0% |
| 19 | Pink (Commercial product G) | 34.7 | 0% |
| 20 | Blue (Commercial product H) | 31.2 | 0% |

With a transmittance of about 75%, 80% of the participants responded that the absorbent article was not visible through the outer surface of the individually packaged product, whereas with a transmittance of up to 60%, 100% of the participants responded that the absorbent article was not visible through the outer surface of the individually packaged product, regardless of the color of the colored part.

REFERENCES SIGNS LIST

1 Individually packaged product
2 Absorbent article
3 Absorbent body
4 Skin contact surface
5 Non-skin-contact surface
6 Packaging sheet
7 Inner surface
8 Outer surface
9 First colored part
10 Tab
11 Pressure-sensitive adhesive part
12 Heat seal
13 Release part
14 Release sheet
15 Second colored part
16 Third colored part

The invention claimed is:

1. An individually packaged product having a folded structure in which an absorbent article is wrapped with a packaging sheet,
wherein the individually packaged product has first to fourth folding lines to form the folded structure in which the first folding line is longitudinally extended in a left side portion of the absorbent article and the packaging sheet, the second folding line is longitudinally extended in a right side portion of the absorbent article and the packaging sheet, the third folding line is laterally extended in the direction perpendicular to the longitudinal direction in a lower end portion of the absorbent article and the packaging sheet, and the fourth folding line is laterally extended in the direction perpendicular to the longitudinal direction in an upper end portion of the absorbent article and the packaging sheet,
wherein a left-hand region of the absorbent article and the packaging sheet is folded along the first folding line and a right-hand region of the absorbent article and the packaging sheet is folded along the second folding line, in sequence, on a middle region defined by the first and second folding lines in such a manner that absorbent article is inwardly folded, and then
a lower region of the absorbent article and the packaging sheet at the lower end portion thereof is folded along the third folding line and an upper region of the absorbent article and the packaging sheet at the upper end portion thereof is folded along the fourth folding line, in sequence, on a middle region defined by the third and fourth folding lines in such a manner that absorbent article is inwardly folded,
wherein as thus folded the packaging sheet has a colored part on an inner surface on the absorbent article side and on an outer surface on the side opposite the inner surface, wherein the colored part on the outer surface of the packaging sheet has a smaller area than the area of the colored part on the inner surface of the packaging sheet, and the colored part is visible through an outer surface of the individually packaged product, but the absorbent article is not visible through the outer surface of the individually packaged product,
wherein the absorbent article has a pressure-sensitive adhesive part on the non-skin-contact surface, the absorbent article is attached to the inner surface of the packaging sheet sandwiching the pressure-sensitive adhesive part, and the absorbent article and packaging sheet is formed by folding the absorbent article inward, and
wherein the absorbent article is easily detached from the inner surface of the packaging sheet.

2. The individually packaged product according to claim 1, wherein the colored part on the inner surface of the packaging sheet further has a detaching function which allows the absorbent article to be easily detached from the packaging sheet.

3. The individually packaged product according to claim 1, wherein the colored part on the inner surface of the packaging sheet is formed by coating the inner surface of the packaging sheet with a single colored material while varying the amount per unit area, and the colored part on the inner surface of the packaging sheet forms a predetermined pattern on the inner surface of the packaging sheet.

4. The individually packaged product according to claim 1, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

5. The individually packaged product according to claim 1, wherein the packaging sheet has the colored part over the entire inner surface on the absorbent article side.

6. The individually packaged product according to claim 1, wherein a release part covers a surface of the colored part on the inner surface of the packaging sheet that contacts with the pressure-sensitive adhesive part.

7. The individually packaged product according to claim 1, wherein a release sheet is bonded to a surface of the colored part on the inner surface of the packaging sheet that contacts with the pressure-sensitive adhesive part.

8. The individually packaged product according to claim 1, wherein the absorbent article further has a colored part on an outer surface of the absorbent article, on the packaging sheet side, the packaging sheet has the colored part on the inner surface of the packaging sheet and colored part on the outer surface of the packaging sheet so that the colored part on the outer surface of the absorbent article is not visible through the outer surface of the individually packaged product.

9. The individually packaged product according to claim 1, wherein the colored part on the inner surface of the packaging sheet is formed by coating the inner surface of the packaging sheet with a single colored material while varying the amount per unit area, and the colored part on the inner surface of the packaging sheet forms a predetermined pattern on the inner surface of the packaging sheet.

10. The individually packaged product according to claim 2, wherein the colored part on the inner surface of the packaging sheet is formed by coating the inner surface of the packaging sheet with a single colored material while varying the amount per unit area, and the colored part on the inner surface of the packaging sheet forms a predetermined pattern on the inner surface of the packaging sheet.

11. The individually packaged product according to claim 1, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

12. The individually packaged product according to claim 2, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

13. The individually packaged product according to claim 3, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

14. The individually packaged product according to claim 9, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

15. The individually packaged product according to claim 10, wherein the colored part on the inner surface of the packaging sheet is formed by coating the inner surface of the packaging sheet with a plurality of colored materials with different colors, and the colored part on the inner surface of the packaging sheet forms a predetermined pattern on the inner surface of the packaging sheet.

16. The individually packaged product according to claim 2, wherein the packaging sheet has the colored part over the entire inner surface on the absorbent article side.

* * * * *